(12) United States Patent
Sastry et al.

(10) Patent No.: US 12,102,344 B2
(45) Date of Patent: Oct. 1, 2024

(54) MEDICAL DEVICE FOR SNARING GUIDEWIRE

(71) Applicant: Myodynamics, LLC, Englewood Cliffs, NJ (US)

(72) Inventors: Ashwani Sastry, Orlando, FL (US); Sreejit Nair, Pembroke Pines, FL (US)

(73) Assignee: MYODYNAMICS, LLC, Englewood Cliffs, NJ (US)

( * ) Notice: Subject to any disclaimer, the term of this patent is extended or adjusted under 35 U.S.C. 154(b) by 72 days.

(21) Appl. No.: 17/347,306

(22) Filed: Jun. 14, 2021

(65) Prior Publication Data

US 2022/0047286 A1 Feb. 17, 2022

Related U.S. Application Data

(60) Provisional application No. 63/063,962, filed on Aug. 11, 2020.

(51) Int. Cl.
| | |
|---|---|
| *A61B 17/221* | (2006.01) |
| *A61M 25/00* | (2006.01) |
| *A61M 25/10* | (2013.01) |
| A61B 17/00 | (2006.01) |

(Continued)

(52) U.S. Cl.
CPC ......... *A61B 17/221* (2013.01); *A61M 25/007* (2013.01); *A61M 25/104* (2013.01); *A61B 2017/00876* (2013.01); *A61B 2017/22038* (2013.01); *A61M 2025/0197* (2013.01)

(58) Field of Classification Search
CPC ........ A61B 17/32056; A61B 2018/141; A61B 2017/00876; A61B 2017/00358; A61B 1/00078; A61M 25/10; A61M 25/104; A61M 25/09041; A61M 29/00; A61M 29/02; A61M 2029/025; A61M 2025/09133; A61F 2/013; A61F 2/011; A61F 2/014; A61F 2/0103
See application file for complete search history.

(56) References Cited

U.S. PATENT DOCUMENTS

| | | | |
|---|---|---|---|
| 4,989,608 A | * | 2/1991 | Ratner .............. A61M 25/0127 600/420 |
| 6,029,671 A | | 2/2000 | Stevens et al. |
| 10,271,762 B2 | | 4/2019 | Grunwald |

(Continued)

*Primary Examiner* — Brooke Labranche
(74) *Attorney, Agent, or Firm* — Evergreen Valley Law Group; Kanika Radhakrishnan

(57) ABSTRACT

Embodiments of the present disclosure provide a medical device for snaring guidewire during endovascular procedure. The medical device includes a catheter and an elongate member. The catheter is deployed into a lumen of a blood vessel through a first vascular access point of a subject. The elongate member includes a distal tip mounted with a first magnetic element and configured to be insertable within the catheter. The elongate member is deployed in the lumen of the blood vessel by advancing through the catheter. The first magnetic element of the elongate member is configured to exert magnetic force to magnetically couple with a guidewire advancing within the lumen through a second vascular access point. The magnetic coupling of the elongate member and the guidewire facilitates attracting the guidewire into the catheter and draw out from the first vascular access point by withdrawing the elongate member while advancing the guidewire.

17 Claims, 7 Drawing Sheets

(51) Int. Cl.
 *A61B 17/22* (2006.01)
 *A61M 25/01* (2006.01)

(56) References Cited

U.S. PATENT DOCUMENTS

| | | |
|---|---|---|
| 10,820,948 B2 | 11/2020 | West et al. |
| 2002/0115986 A1 | 8/2002 | Shadduck |
| 2005/0107867 A1* | 5/2005 | Taheri .............. A61B 17/12022 623/1.38 |
| 2005/0251197 A1* | 11/2005 | Hensley ........... A61B 17/32056 606/200 |
| 2006/0149295 A1* | 7/2006 | Fleming, III .... A61B 17/32056 606/113 |
| 2008/0091264 A1* | 4/2008 | Machold ............... A61M 25/09 623/2.1 |
| 2008/0221656 A1 | 9/2008 | Hartley et al. |
| 2010/0256601 A1* | 10/2010 | Lippert ............. A61M 25/0051 604/523 |
| 2012/0296620 A1 | 11/2012 | Aulbach |
| 2014/0066970 A1 | 3/2014 | Warren |

* cited by examiner

MEDICAL DEVICE FOR SNARING GUIDEWIRE

TECHNICAL FIELD

The present disclosure relates to a medical device for endovascular procedures and, more particularly relates, to a medical device including magnetic materials for snaring guidewires during endovascular procedures.

BACKGROUND

Endovascular surgery is one of the procedures undertaken by clinicians that utilizes relevant anatomic knowledge along with minimally invasive techniques. A clinician makes use of surgical instruments to treat arteries and veins within the body. The arteries and veins can be in the peripheral vasculature (legs, arms, abdomen), cerebral vasculature, or cardiac vasculature (coronary arteries, coronary veins). The surgical instruments (e.g., catheters, introducer sheaths, and stylettes) are manually inserted into the body and manipulated by the surgeon using two degrees of freedom—advancing/retracting, and clockwise and counterclockwise rotation. As endovascular procedures have become more mainstream and more complex, procedure duration has increased significantly. One of the more complex techniques in endovascular surgery is to cross an occluded blood vessel (arterial or venous) from two different directions and meet in the middle. In this technique, a wire inserted from one side of the body must be exteriorized or "flossed" and pulled out from another location in the body. Manual steering of the surgical instruments in the blood vessels to achieve this can be challenging, time-intensive, and require significant skill.

Therefore, there is a need for techniques to overcome one or more limitations stated above in addition to providing other technical advantages.

SUMMARY

Various embodiments of the present disclosure provide a medical device for snaring a guidewire during endovascular procedure.

In an embodiment, a medical device is disclosed. The medical device includes a catheter including a proximal portion, a distal portion and a hollow cavity extending therebetween. The distal portion of the catheter is configured to be deployed into a lumen of a blood vessel by advancing the catheter through a first vascular access point of a subject. Further, the medical device includes an elongate member including a distal tip portion mounted with a first magnetic element and configured to be insertable within the catheter. The distal tip portion of the elongate member is configured to be deployed in the lumen of the blood vessel by advancing the elongate member through the catheter deployed in the lumen of the blood vessel through the first vascular access point. The first magnetic element of the elongate member is configured to exert magnetic force to magnetically couple with a guidewire advancing within the lumen of the blood vessel through a second vascular access point of the subject. The magnetic coupling of the elongate member and the guidewire facilitates attracting pulling the guidewire into the catheter and draw out from the first vascular access point by simultaneously withdrawing the elongate member from the first vascular access point and advancing the guidewire through the second vascular access point.

In another embodiment, a medical device for snaring a guide wire during endovascular procedure is disclosed. The medical device includes a catheter including a proximal portion, a distal portion and a hollow cavity extending therebetween. The distal portion of the catheter is configured to be deployed into a subintimal space of an occlusion of a blood vessel by advancing the catheter through a first vascular access point of a subject. Further, the medical device includes an elongate member including a distal tip portion mounted with a first magnetic element and configured to be insertable within the catheter. The distal tip portion of the elongate member is configured to be deployed in the subintimal space of the occlusion by advancing the elongate member through the catheter deployed in the subintimal space through the first vascular access point. The first magnetic element of the elongate member is configured to exert magnetic force to magnetically couple with the guidewire advancing within the subintimal space of the blood vessel through a second vascular access point of the subject. The magnetic force exerted by the first magnetic element enables the guidewire, the elongate member and the catheter to penetrate through tissue in the subintimal space of the blood vessel keeping the guidewire and the elongate member apart from each other for magnetic coupling. The magnetic coupling of the elongate member and the guidewire facilitates attracting the guidewire into the catheter and draw out from the first vascular access point by simultaneously withdrawing the elongate member from the first vascular access point and advancing the guidewire through the second vascular access point.

In yet another embodiment, a medical device for snaring a guide wire during endovascular procedure is disclosed. The medical device includes a catheter including a proximal portion, a distal portion and a hollow cavity extending therebetween. The distal portion of the catheter is mounted with a second magnetic element and configured to be deployed into a lumen of a blood vessel by advancing the catheter through a first vascular access point of a subject. The second magnetic element of the catheter is configured to exert magnetic force to magnetically couple with the guidewire advancing within the lumen of the blood vessel through a second vascular access point of the subject. Further, the magnetic force exerted by the second magnetic element attracts the guidewire into the catheter and enables the guidewire to be drawn out from the first vascular access point by advancing the guidewire from the second vascular access point.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1A:
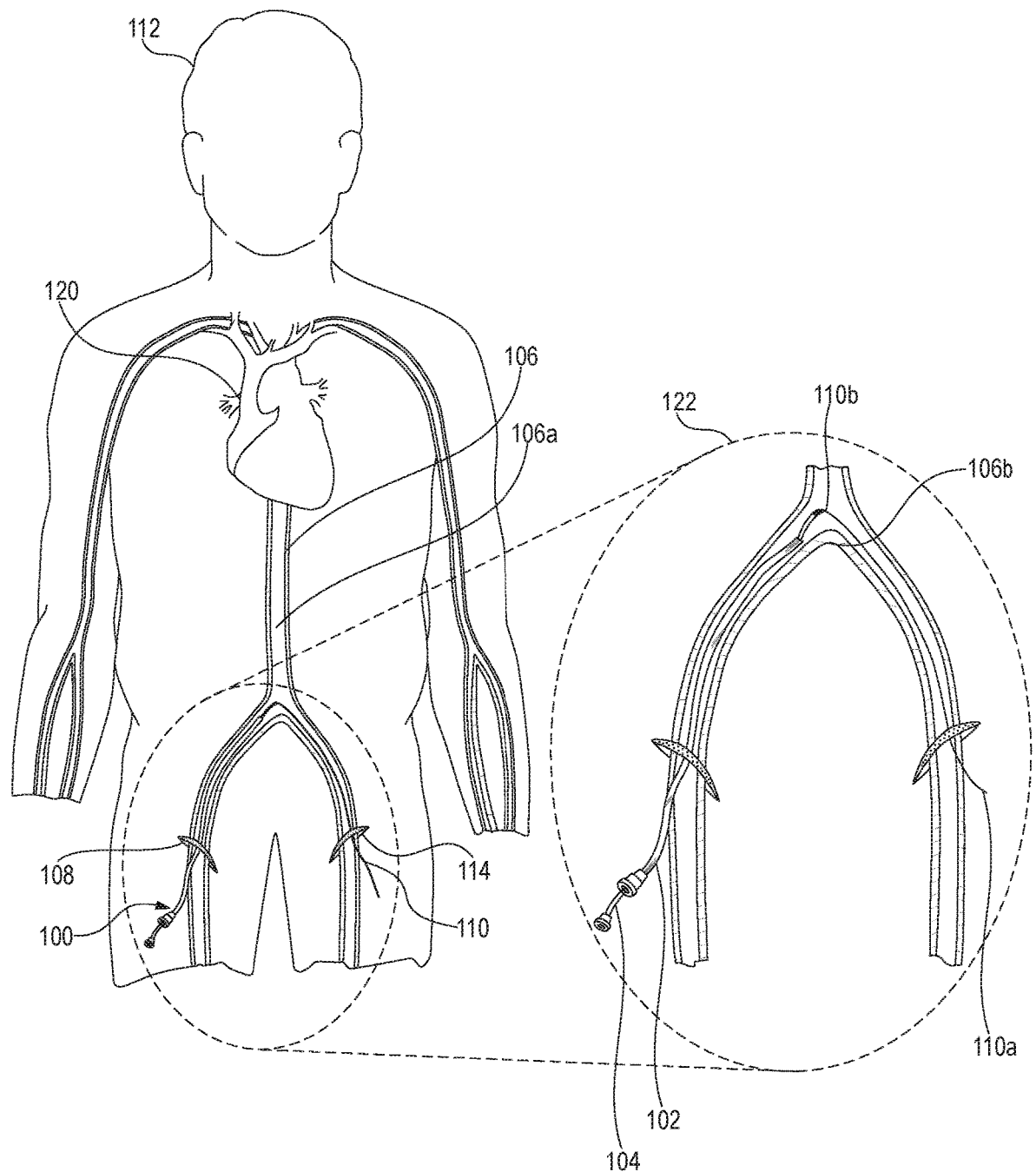
FIG. 1A illustrates a schematic view of a medical device inserted into a subject for snaring a guidewire during an endovascular procedure with a magnified view of magnetic coupling between an elongate member of the medical device and a guidewire, in accordance with an example embodiment of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various embodiments of the present disclosure provide a medical device for snaring a guidewire during an endovascular procedure. In one embodiment, the medical device includes a catheter and an elongate member. Further, the catheter includes a proximal portion, a distal portion, and a hollow cavity extending therebetween. The distal portion of the catheter is deployed into a lumen of a blood vessel by advancing the catheter through a first vascular access point of a subject. The elongate member includes a distal tip portion mounted with a first magnetic element. The elongate member is inserted into the catheter and advanced into the lumen of the blood vessel through the first vascular access point. The elongate member is deployed in the lumen such that a proximal tip portion of the elongate member is located outside the subject. The elongate member may include one of a stylet, a dilator, a needle, or another guidewire. The first magnetic element of the elongate member is configured to exert magnetic force to magnetically couple with a distal end of a guidewire advancing within the lumen of the blood vessel through a second vascular access point of the subject. Further, the magnetic force exerted by the first magnetic element may enable the guidewire, the elongate member, and the catheter to penetrate through tissue in a subintimal space of the blood vessel keeping the guidewire and the elongate member apart from each other for magnetic coupling. The magnetic coupling of the elongate member and the guidewire facilitate pulling the guidewire into the catheter by withdrawing the elongate member while advancing the guidewire. As the elongate member is withdrawn while the guidewire is advanced, the guidewire is pulled through the catheter and ultimately through the first vascular access point and outside of the body.

In an embodiment, the catheter may include a side hole configured proximate to the distal portion. The side hole allows a passageway for the elongate member deployed in the catheter. The catheter is advanced into the subintimal space of an occlusion. The elongate member deployed in the catheter is advanced through the side hole of the catheter to penetrate the subintimal space of the occlusion. The elongate member then magnetically couples with the guidewire advancing within the lumen through the second vascular access point. More specifically, the magnetic force exerted by the first magnetic element of the elongate member magnetically captures the guidewire, which can then be passed into the catheter by simultaneously withdrawing the elongate member and advancing the guidewire.

In another embodiment, the catheter may include a second magnetic element mounted at the distal portion. The second magnetic element at the distal portion eliminates the usage of the elongate member for snaring the guidewire during the endovascular procedure. The catheter deployed in the blood vessel by advancing through the first vascular access point is configured to magnetically couple with the guidewire advancing within the lumen through the second vascular access point. More specifically, the second magnetic element is configured to exert magnetic force to magnetically couple with the guidewire advanced into the blood vessel from a second vascular access point. In yet another embodiment, the catheter may be a balloon angioplasty catheter. In this configuration, the catheter may include an inflatable balloon located proximate to the distal portion of the catheter. Further, the inflatable balloon may be filled with ferromagnetic fluid. The ferromagnetic fluid is configured to exert a magnetic force for attracting the guidewire advancing within the blood vessel.

Further, the medical device may include an introducer sheath configured to be inserted into the blood vessel of the subject through the first vascular access point. The introducer sheath may include a third magnetic element mounted to a secondary portion of the introducer sheath. The introducer sheath mounted with the third magnetic element may be configured to snare the guidewire advancing through the second vascular access point during the endovascular procedure.

Various embodiments of a medical device for snaring guidewire during endovascular procedure are described with reference to FIGS. 1A-1B to FIG. 6.

Figure 1B:
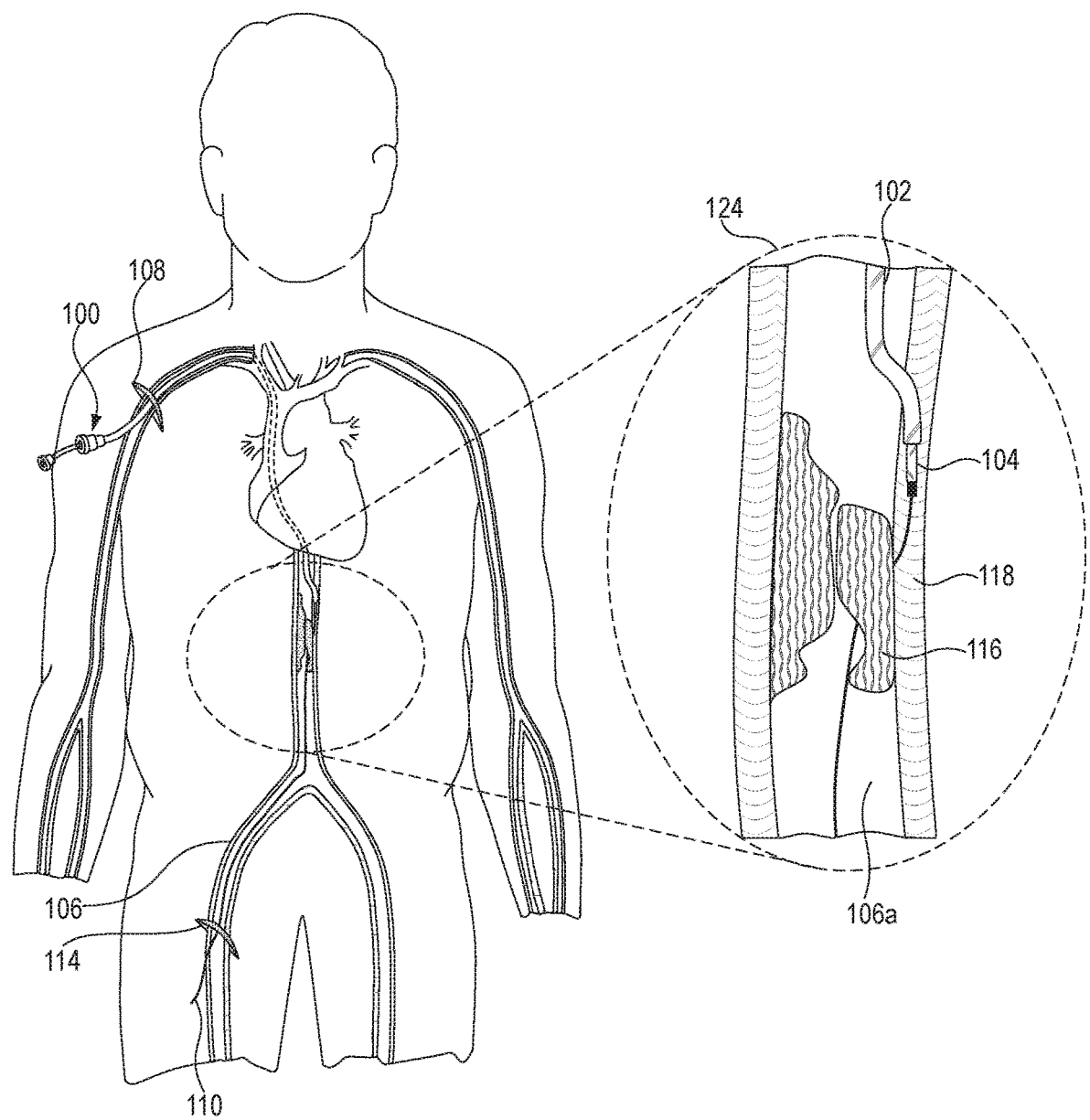
FIG. 1B illustrates a schematic view of the medical device inserted into the subject for snaring the guidewire during the endovascular procedure with a magnified view of magnetic coupling between the elongate member of the medical device and the guidewire, in accordance with an example embodiment of the present disclosure.

FIGS. 1A and 1B illustrate a schematic view of a medical device 100 inserted into a subject for performing endovascular procedures, in accordance with an example embodiment of the present disclosure. The medical device 100 is inserted into a lumen 106a of a blood vessel 106 to snare a guidewire during an endovascular procedure.

As shown in FIG. 1A, the medical device 100 is deployed into the lumen 106a of the blood vessel 106 through a first vascular access point 108 of a subject 112. As an example, the medical device 100 deployed in the blood vessel 106 is a femoral artery. The femoral artery is a common access site for performing cardiac catheterization. More specifically, the medical device 100 inserted into the lumen 106a of the blood vessel 106 provides access to an internal organ 120 such as the heart.

The medical device 100 includes a catheter 102 and an elongate member 104. The catheter 102 is inserted into the blood vessel 106 (e.g., the femoral artery) through the first vascular access point 108. The elongate member 104 is configured to be insertable within the catheter 102. Further, a guidewire 110 including a proximal end 110a and a distal end 110b is inserted into the lumen 106a of the blood vessel 106 through a second vascular access point 114 of the subject 112. The distal end 110b of the guidewire 110 is disposed in the lumen 106a when advanced through the second vascular access point 114, while the proximal end 110a is located outside the subject 112. It should be noted that the first vascular access point 108 and the second vascular access point 114 are two different access points in the body of the subject 112. For example, the first vascular access point 108 that provides passage for the catheter 102, and the elongate member 104 may be the right groin area of the subject 112. The second vascular access point 114 that provides passage for the guidewire 110 may be the left groin area of the subject 112. Alternatively, the first vascular access point may be the right femoral artery of the subject, and the 2$^{nd}$ vascular access point may be the right dorsalis pedis artery of the subject. The first vascular access point 108 and the second vascular access point 114 providing passage for the medical device 100 and the guidewire 110 to access the blood vessel 106 may vary based on the procedures involved in treating the internal organ 120 or the blood vessel 106. For example, when treating the coronary vasculature of the heart 120, the first vascular access point may be the right groin, with the medical device 100 passing into the right coronary artery, while the second vascular access point 108 may be the left groin with the guidewire 110a being passed through the left coronary artery, through septal collaterals, and into the right coronary artery where the device 100 sits.

The elongate member 104 inserted into the catheter 102 is deployed into the lumen 106a of the blood vessel 106 by advancing the elongate member 104 through the first vascular access point 108. In other words, the elongate member 104 is advanced till a bifurcation 106b of the femoral artery through the first vascular access point 108. Further, the guidewire 110, advanced through the second vascular access point 114, is positioned proximate to the bifurcation 106b. The elongate member 104 mounted with a first magnetic element (see, 212 of FIG. 2B) is configured to magnetically capture the guidewire 110 advancing within the lumen 106a through the second vascular access point 114. This enables a magnetic coupling of the elongate member 104 and the guidewire 110 (see, magnified view 122 of FIG. 1A).

In an example scenario, an occlusion 116 may be present in the lumen 106a of the blood vessel 106 (e.g., as shown in FIG. 1B). In such scenario, the mobility of the catheter 102, the elongate member 104 and the guidewire 110 to the target site may be hindered. However, the hindrance due to the occlusion 116 in the lumen 106a is dominated by the effect of a first magnetic force exerted by the first magnetic element 212 of the elongate member 104. It should be noted that the first vascular access point 108 and the second vascular access point 114 are a chest area and the leg groin area of the subject 112 respectively (e.g., as shown in FIG. 1B). The first magnetic force exerted by the first magnetic element 212 facilitates the guidewire 110 to penetrate through the tissue of the blood vessel 106 and enter a subintimal space 118 of the blood vessel 106 that the elongate member 104 occupies to magnetically couple with the elongate member 104 (see, magnified view 124 of FIG. 1B). The magnetic interaction between the elongate member 104 and the guidewire 110 allows crossing of the occlusion 116 in the blood vessel 106 and to reach the target site.

Figure 2A:
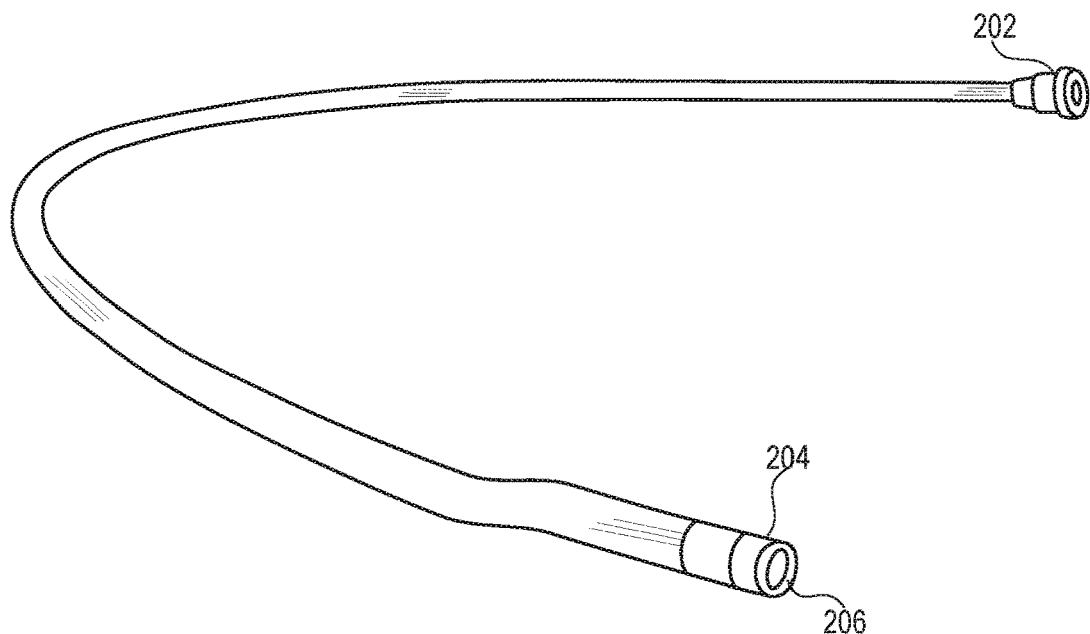
FIG. 2A is a perspective view of a catheter, in accordance with an example embodiment of the present disclosure.

Referring now to FIG. 2A, in conjunction with FIGS. 1A and 1B, the catheter 102 is a flexible tube including a proximal portion 202 and a distal portion 204 and a hollow cavity 206 extending therebetween. The catheter 102 is formed as an elongate member 104. The flexibility of the catheter 102 provides the ability to steer the catheter 102 in the blood vessel 106 through the first vascular access point 108 and deploy in the target site. The distal portion 204 may be angled allowing further ability to direct and steer the catheter 102 (e.g., as shown in FIG. 2A). The hollow cavity 206 allows passageway for the intervention tools (such as the elongate member 104, guidewires, etc.) from within the catheter 102 to the target site of intervention within the blood vessel 106. The distal portion 204 of the catheter 102 is deployed in the lumen 106a of the blood vessel 106 when advanced through the first vascular access point 108, while the proximal portion 202 is located outside the subject 112. In one configuration, the catheter 102 may include side holes at the distal portion 204 which is further explained in detail with reference to FIG. 3.

The catheter 102 may be made of materials such as, but not limited to, synthetics such as PTFE, radiopaque materials including specific radiopaque markers at designated locations, and polyurethane. In one embodiment, the catheter 102 may be made of reinforcing materials or may contain metal braiding that provide kinking or crush resistance to the catheter 102. Further, the reinforcing materials may be magnetic resonance imaging (MRI) compatible that facilitate navigation of the catheter 102 when advanced into the lumen 106a of the blood vessel 106. For example, the reinforcing materials may be one of a non-ferrous materials, polyester microelement, a monofilament material and the like. The catheter 102 may be configured with dimensions in conformity with the dimensions of the lumen 106a, which eases the movement of the catheter 102 within the lumen 106a. Further, the hollow cavity 206 may be configured with the dimensions in conformity with dimensions of the elongate member 104. The length dimension of the catheter 102 depends on the distance of the target site. For example, the length dimension of the catheter 102 may range from 10 centimeters to 150 centimeters.

Figure 2B:
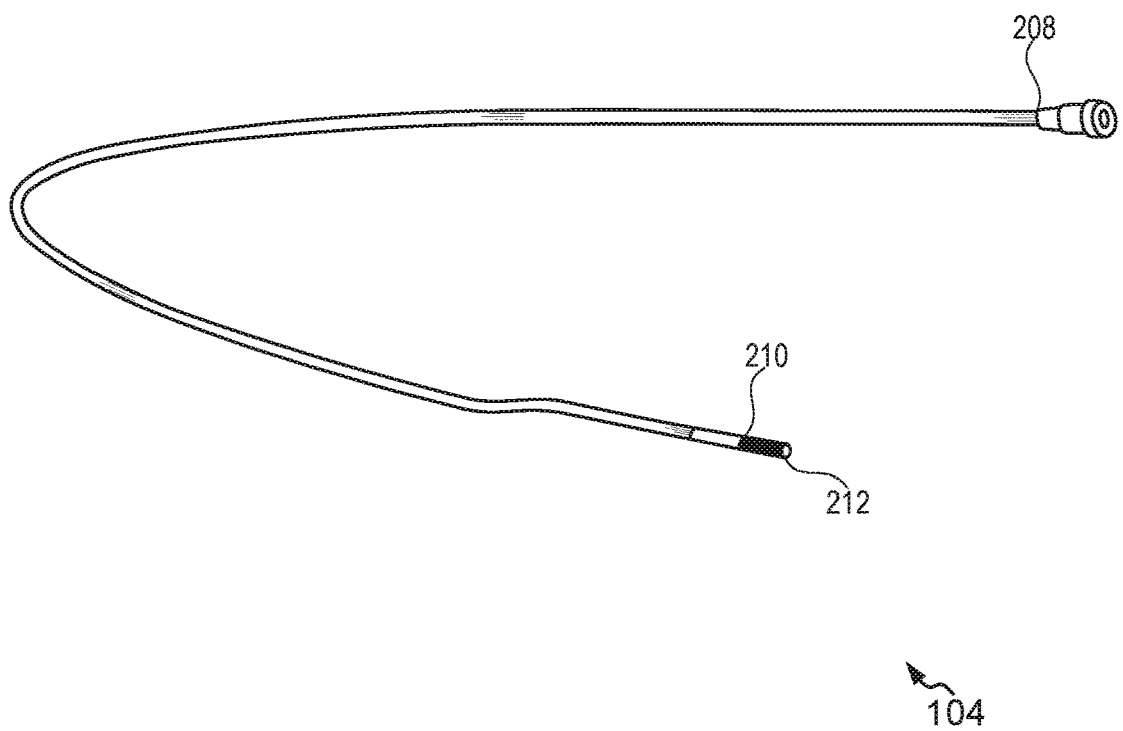
FIG. 2B is a perspective view of the elongate member, in accordance with an example embodiment of the present disclosure.

Referring now to FIG. 2B, in conjunction with FIGS. 1A and 1B, the elongate member 104 includes a proximal tip portion 208 and a distal tip portion 210. The elongate member 104 may be a solid component (stylette), or it may include a hollow cavity extending along a length of the elongate member 104 which can accommodate a guidewire, such as the guidewire 110. The elongate member 104 may be angled allowing further ability to direct and steer the elongate member 104 within the catheter 102 (e.g., as shown in FIG. 2B). The elongate member 104 may be a stylet that is inserted into the catheter 102 during the endovascular procedures. Additionally, or alternatively, the elongate member 104 may be a dilator, a metallic wire, or a needle. The elongate member 104 may be made of materials that are more rigid than the catheter 102. For example, the elongate member 104 may be formed using materials such as but not limited to polycarbonate, or may be braided with metallic wire. Further, the outer diameter of the elongate member 104 is selected based on the inner diameter of the catheter 102. The outer diameter of the elongate member 104 is less than the inner diameter of the catheter 102, so the elongate member 104 can easily slide into and out of the catheter 102.

The elongate member 104 is inserted into the catheter 102 and deployed into the lumen 106a and the subintimal space 118 by advancing through the first vascular access point 108. More specifically, the elongate member 104 is deployed in the lumen 106a, such that the distal tip portion 210 is disposed in the lumen 106a and the proximal tip portion 208 is located outside of the subject 112 (e.g., as shown in FIGS. 1A and 1B). In other words, the elongate member 104 is long enough to extend along the length of the catheter 102 and beyond the distal portion 204 of the catheter 102. The elongate member 104 facilitates guidance of the catheter 102 during its placement in the lumen 106a.

The distal tip portion 210 of the elongate member 104 is mounted with the first magnetic element 212. The first magnetic element 212 at the distal tip portion 210 may be a single magnet. Additionally, or alternatively, the first magnetic element 212 may be formed by stacking a plurality of magnetic elements. The first magnetic element 212 may be configured with the dimensions in conformity with the dimensions of the distal tip portion 210 of the elongate member 104 so as to ensure a snug mount of the first magnetic element 212 at the distal tip portion 210. The first magnetic element 212 may be mounted to the distal tip portion 210 by using conventional mounting means. In an embodiment, the first magnetic element 212 may be inserted into the elongate member 104 and mounted proximate to the distal tip portion 210. As such, the mounting of the first magnetic element 212 may seal an opening of the distal tip portion 210 of the elongate member 104. In another embodiment, the first magnetic element 212 may be mounted on the outer surface of the elongate member 104 proximate to the distal tip portion 210.

The first magnetic element 212 mounted at the distal tip portion 210 may be a permanent magnet (e.g., ferromagnetic material), a rare earth metal (e.g., Neodymium, Samarium Cobalt) and the like. In this configuration, the first magnetic element 212 is configured to exert the first magnetic force without any external actuation (such as electrical or mechanical power). As such, the elongate member 104 mounted with the first magnetic element 212 is referred to as passive magnetic instrument. Further, a region proximate to the distal tip portion 210 mounted with the first magnetic element 212 may be formed of a softer material than the rest of the elongate member 104. This configuration allows the distal tip portion 210 to be atraumatic and further allows the first magnetic element 212 to have dominating effect on maneuverability and guidance. The first magnetic element 212 remains magnetized to attract the magnetically attractive elements i.e. the guidewire 110 deployed in the lumen 106a and positioned proximate to the distal tip portion 210 of the elongate member 104. Further, the first magnetic element 212 must be magnetized suitably such that the elongate member 104 and the guidewire 110 are not decoupled during maneuverability. It should be noted that the guidewire 110 may be any standard guidewire available off the shelf, and that the magnetic strength of first magnetic element 212 is sufficient to attract the "off the shelf" guidewire.

Alternatively, the first magnetic element 212 mounted at the distal tip portion 210 may be an electromagnet. In one embodiment, the first magnetic element 212 may be mounted at one or more locations along the length of the elongate member 104. Mounting the first magnetic element 212 at more than one location provides large magnetic force to attract the guidewire 110 advancing from opposite direction (i.e. the second vascular access point 114).

Referring back to FIG. 1A, the catheter 102 along with the elongate member 104 deployed in the lumen 106a by advancing through the first vascular access point 108 is configured to snare the guidewire 110. Particularly, the first magnetic element 212 at the distal tip portion 210 of the elongate member 104 is configured to exert the first magnetic force which attracts the distal end 110b of the guidewire 110 disposed in the lumen 106a and positioned proximate to the distal tip portion 210 of the elongate member 104 (see, the magnified view 122 of FIG. 1A). In addition, the first magnetic element 212 inducing the first magnetic force may result in propagation of the elongate member 104 towards the guidewire 110 for magnetic coupling. In other words, the first magnetic force enables the distal tip portion 210 of the elongate member 104 to reach difficult positions (i.e., the bifurcations 106b) within the vasculature. The propagation of the elongate member 104 due to the first magnetic force (i.e., Lorentz force) may enable the elongate member 104 and the catheter 102 to achieve desired configuration for attracting the guidewire 110. Further, the magnetic coupling between the elongate member 104 and the guidewire 110 facilitates exteriorization of the guidewire 110 from the first vascular access point 108. More specifically, the magnetic coupling of the elongate member 104 and the guidewire 110 facilitates attracting the guidewire 110 into the catheter 102 and draw out from the first vascular access point 108 by simultaneously withdrawing the elongate member 104 from the first vascular access point 108 and advancing the guidewire 110 through the second vascular access point 114.

Referring back to FIG. 1B, the catheter 102 may be deployed in the subintimal space 118 of the occlusion 116 by advancing through the first vascular access point 108. Further, the elongate member 104 may be deployed in the subintimal space 118 of the occlusion 116 by advancing the elongate member 104 through the catheter 102 deployed in the subintimal space 118 through the first vascular access point 108. As such, the first magnetic element 212 of the elongate member 104 is configured to exert the first magnetic force to magnetically couple with the guidewire 110 advancing within the lumen 106a through the second vascular access point 114. The first magnetic force exerted by the first magnetic element 212 facilitates the guidewire 110, the catheter 102 and the elongate member 104 to penetrate through the tissue of the subintimal space 118 keeping the guidewire 110 and the elongate member 104 apart from each other for magnetic coupling, thereby indicating successful crossing of the occlusion 116 (see, magnified view 124 of FIG. 1B). The magnetic coupling of the elongate member 104 and the guidewire 110 facilitates attracting the guidewire 110 into the catheter 102 and draw out from the first vascular access point 108 by simultaneously withdrawing the elongate member 104 from the first vascular access point 108 and advancing the guidewire 110 through the second vascular access point 114.

Figure 3:
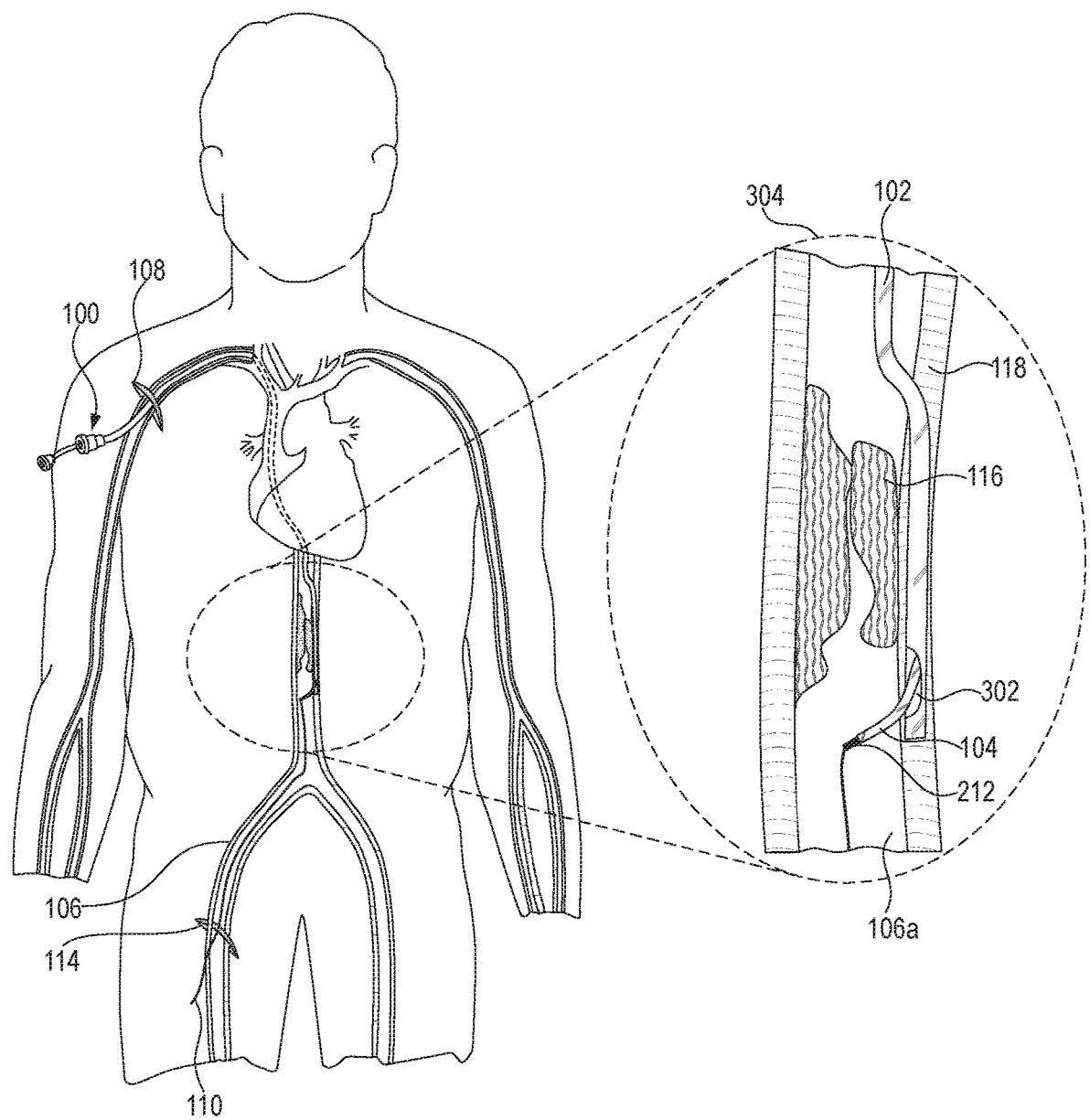
FIG. 3 illustrates a schematic view of the medical device inserted into the subject for snaring the guidewire during the endovascular procedure with a magnified view of magnetic coupling between the elongate member of the medical device and the guidewire, in accordance with an example embodiment of the present disclosure.

FIG. 3 illustrates magnetic snaring of the guidewire 110 by the elongate member 104 during the endovascular procedure, in accordance with an example embodiment of the present disclosure. As shown in FIG. 3, the distal portion 204 of the catheter 102 is configured with a side hole 302. The side hole 302 is configured to allow a passageway for the elongate member 104 therein. The catheter 102 including the side hole 302 is referred to as a re-entry device. In this configuration, the elongate member 104 insertable within the catheter 102 may be a magnetic needle. The magnetic needle may be flexible so as to adjust to the structure of the catheter 102 deployed in the lumen 106a of the blood vessel 106. Further, the region proximate to the distal tip portion 210 of the elongate member 104 may be curved or angled, such that it allows an easy passage of the elongate member 104 through the side hole 302 of the catheter 102 (e.g., as shown in enlarged portion 304). The distal tip portion 210 of the elongate member 104 may be sharp and mounted with the first magnetic element 212, as explained above with reference to FIG. 2B.

The catheter 102 and the elongate member 104 are advanced into the lumen 106a through the first vascular access point 108 and deployed in the subintimal space 118 of the blood vessel 106 (e.g., as shown in FIG. 3). Further, the guidewire 110 is advanced into the lumen 106a through the second vascular access point 114 and positioned proximate to the elongate member 104 in the lumen 106a. The first magnetic element 212 at the distal tip portion 210 is configured to exert the first magnetic force for attracting the guidewire 110. The first magnetic force facilitates the elongate member 104 to pass through the side hole 302 and pierce through the tissue of the subintimal space 118 or the occlusion 116 separating the elongate member 104 and the guidewire 110 for magnetic coupling. In other words, the elongate member 104 deployed in the subintimal space 118 is pulled towards the lumen 106a for magnetically coupling with the guidewire 110, thereby indicating a successful crossing of an occlusion 116 in the blood vessel 106 in a more efficient manner (see, the enlarged portion 304 of FIG. 3). Further, the magnetic coupling of the elongate member 104 and the guidewire 110 enables exteriorization of the guidewire 110 through the first vascular access point 108 as explained with reference to FIGS. 1A and 1B.

In one embodiment, the distal end 110b of the guidewire 110 may be configured with the magnetic element, such as the first magnetic element 212. As such, the resultant first magnetic force of the elongate member 104 and the guidewire 110 is a pure torque, which allows a degree of freedom (DoF) actuation sufficient for the deflection of the distal tip portion 210 of the elongate member 104. The deflection allows the elongate member 104 to pass through the side hole 302 and enter the lumen 106a by penetrating the tissue of the subintimal space 118 to magnetically couple with the guidewire 110. The magnetic coupling facilitates crossing of the occlusion 116 in the blood vessel 106 as explained above.

In another embodiment, a catheter, such as the catheter 102 may be advanced into the subintimal space 118 for allowing passage of elongate member 104 (e.g., a wire with a distal magnetic tip). The wire with the distal magnetic tip inserted within the catheter 102 and deployed in the subintimal space 118 or lumen 106a is configured to magnetically capture the guidewire 110 advancing through the second vascular access point 114. In this scenario, the wire may be configured with diameter of either 014 inch, 018 inch, 035 inch, or any other diameter as per feasibility and requirement.

Figure 4A:
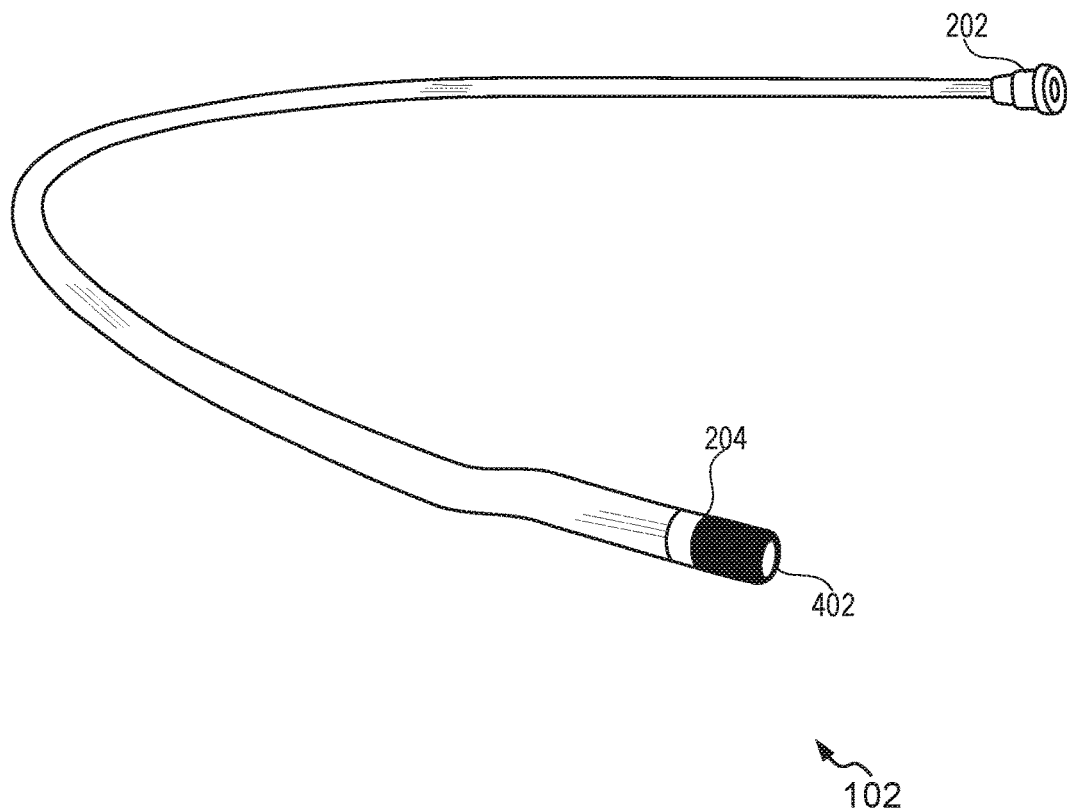
FIGS. 4A-4B illustrate the catheter for magnetic snaring of the guidewire during the endovascular procedure, in accordance with an example embodiment of the present disclosure.
Figure 4B:
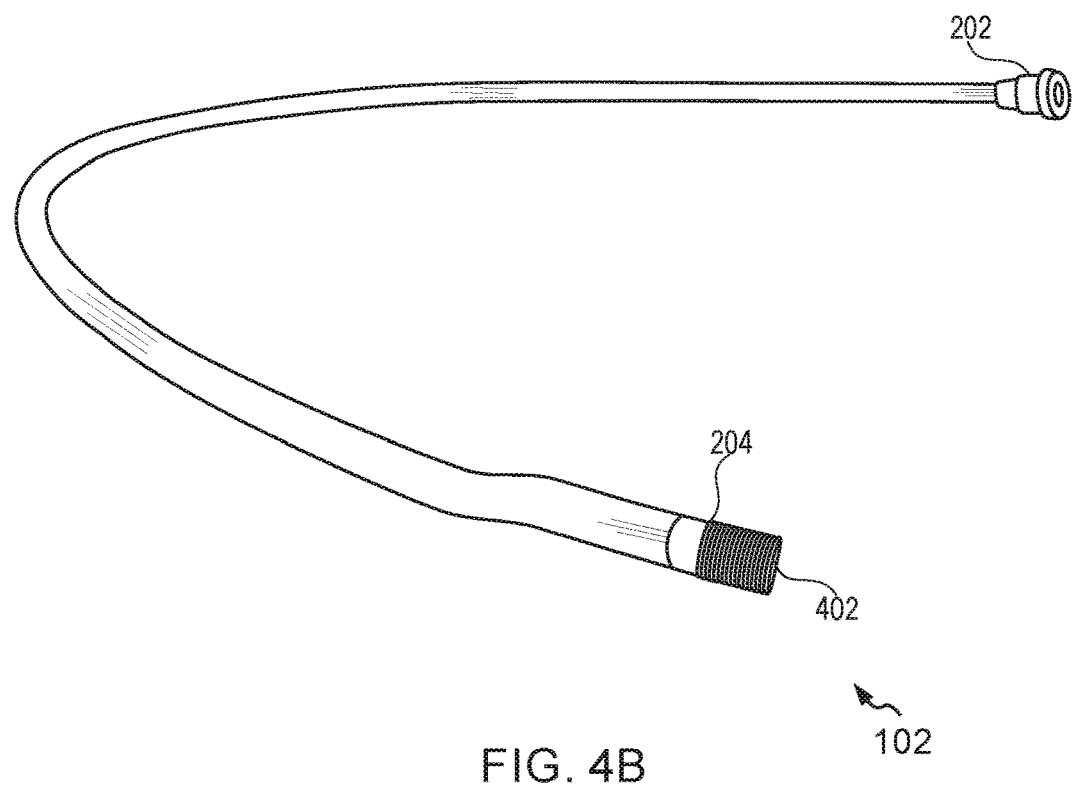

FIGS. 4A-4B illustrate a catheter for magnetic snaring of a guidewire, such as the guidewire 110 during the endovascular procedure, in accordance with an example embodiment of the present disclosure.

As shown in FIG. 4A, the catheter 102 includes a second magnetic element 402 mounted to an opening (not shown in FIGS.) at the distal portion 204. The second magnetic element 402 exhibits similar properties as that of the first magnetic element 212 which is explained with reference to FIG. 2B. The catheter 102 mounted with the second magnetic element 402 is referred to as the passive magnetic instrument. This configuration of the catheter 102 mitigates the use of the elongate member 104 for snaring guidewire 110. The second magnetic element 402 mounted to the opening at the distal portion 204 may be the permanent magnet, the rare earth metal, the ferromagnetic material and the like. Additionally or alternatively, the second magnetic element 402 may be an electromagnet (e.g., a coil or a solenoid) which is explained with reference to FIG. 4B.

As shown in FIG. 4B, the second magnetic element 402 is an electromagnet (depicted as the solenoid or the coil mounted at the distal portion 204). In this configuration, the second magnetic element 402 is magnetized by using external actuation system (e.g., electrical or mechanical power). For example, the second magnetic element 402 may be connected to an electrical power source via a current carrying wire (not shown in FIGS.) passing within the hollow cavity 206 of the catheter 102. The second magnetic element 402 exerts a second magnetic force based on receiving the electric current. Further, the magnetization strength may be varied by adjusting the amount of electric current supplied to the second magnetic element 402. In this configuration, the second magnetic element 402 is kept actuated until the catheter 102 and the guidewire 110 cross the bifurcation 106b or the occlusion 116 in the blood vessel 106. In an embodiment, the second magnetic element 402 may be actuated by using an external permanent magnet.

The catheter 102 mounted with the second magnetic element 402 is advanced through the first vascular access point 108 such that the proximal portion 202 is located outside the subject 112. The second magnetic element 402 exerts the second magnetic force to attract the guidewire 110 advancing in the lumen 106a through the second vascular access point 114. The magnetic coupling between the catheter 102 and the guidewire 110 facilitates crossing of the bifurcation 106b or the occlusion 116 present in the blood vessel 106. Further, the magnetic coupling of the elongate member 104 and the guidewire 110 enables the guidewire 110 to be pulled through the first vascular access point 108 and outside of the subject 112 as explained with reference to FIGS. 1A and 1B.

Figure 5A:
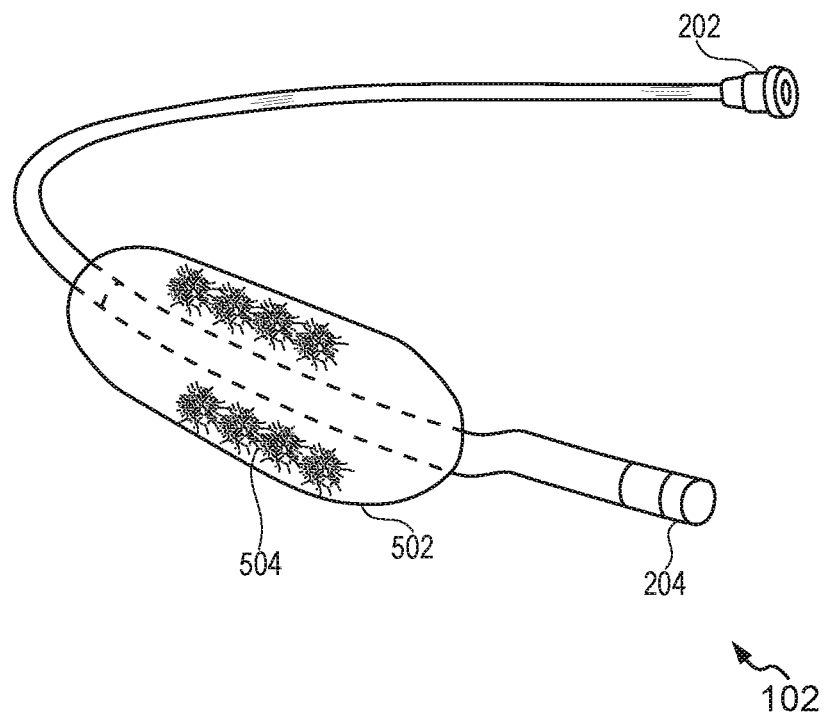
FIGS. 5A-5B illustrate the catheter for magnetic snaring of the guidewire during the endovascular procedure, in accordance with an example embodiment of the present disclosure.

FIG. 5A illustrates a catheter for magnetic snaring of a guidewire, such as the guidewire 110 during the endovascular procedure, in accordance with another example embodiment of the present disclosure. As shown in FIG. 5, the catheter 102 includes an inflatable balloon 502 located proximate to the distal portion 204. The catheter 102 with the inflatable balloon 502 is referred to as a balloon angioplasty catheter. The inflatable balloon 502 may be filled with ferromagnetic fluid 504. The ferromagnetic fluid 504 is configured to exert a fourth magnetic force to magnetically couple with the guidewire 110. In other words, the guidewire 110 enters the hollow cavity 206 due to the fourth magnetic force exerted by the ferromagnetic fluid 504. The guidewire 110 enters the hallow cavity 206 until a region in which the ferromagnetic fluid 504 is located in the catheter 102 by penetrating through the occlusion 116. The magnetic coupling facilitates crossing of the occlusion 116 in the blood vessel 106.

Figure 5B:
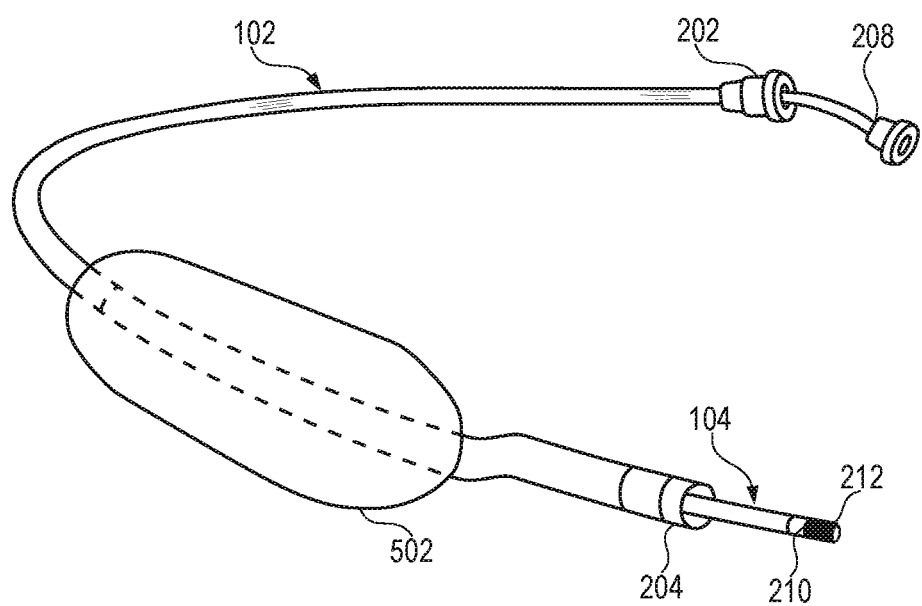

Referring now to FIG. 5B, the catheter 102 (i.e., the balloon angioplasty catheter) may be configured to receive an elongate member, such as the elongate member 104. In this configuration, the elongate member 104 may be a dilator. The dilator is inserted in the hollow cavity 206 of the catheter 102. The elongate member 104 mounted with the first magnetic element 212 is configured to inflate the balloon 502 located at the distal portion 204. Inflating the balloon 502 results in deformation of the occlusion 116 and provides a passageway for the catheter 102, the elongate member 104 and the guidewire 110 in the lumen 106a for magnetic coupling. Further, the first magnetic force exerted by the first magnetic element 212 facilitates magnetic coupling of the elongate member 104 and the guidewire 110 advancing within the lumen 106a through the vascular access points 108 and 114 respectively, thereby indicating successful crossing of the occlusion 116.

In an embodiment, the catheter 102 may include an expandable occlusive mesh (not shown in FIGS.) mounted to the inflatable balloon 502. The elongate member 104 (i.e., the dilator) may be configured to inflate the balloon 502 such that the expandable occlusive mesh expands radially, thus causing deformation of the occlusion 116 in the lumen 106a of the blood vessel 106.

Figure 6:
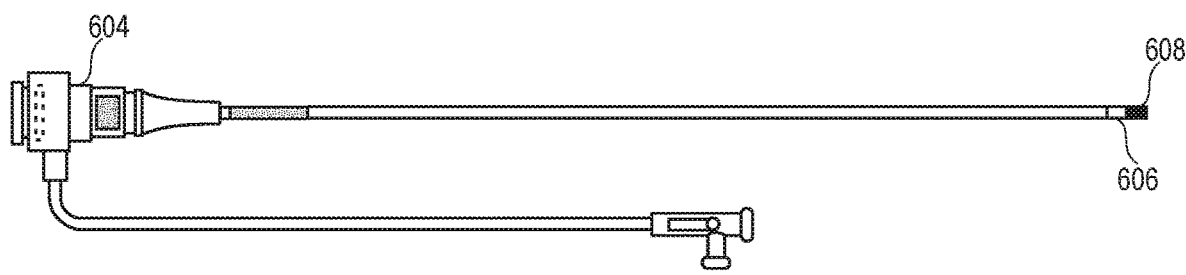
FIG. 6 illustrates an introducer sheath for magnetic snaring of the guidewire during the endovascular procedure, in accordance with an example embodiment of the present disclosure.

FIG. 6 illustrates an introducer sheath 602 for snaring a guidewire, such as the guidewire 110 during the endovascular procedure, in accordance with an example embodiment of the present disclosure. As shown in FIG. 6, the introducer sheath 602 includes a primary portion 604 and a secondary portion 606. The introducer sheath 602 is configured to receive a catheter, such as the catheter 102 for inserting into a body of the subject 112.

The secondary portion 606 of the introducer sheath 602 is mounted with a third magnetic element 608. This configuration of the introducer sheath 602 mitigates the use of the catheter 102 for snaring the guidewire 110 advancing within the blood vessel 106 through the second vascular access point 114. In other words, the catheter 102 may be substituted by using the introducer sheath 602 mounted with the third magnetic element 608 for snaring the guidewire 110 during the endovascular procedures. The third magnetic element 608 may be, but not limited to, the permanent magnet, the rare earth metal, the ferromagnetic material and the electromagnet. Further, the third magnetic element 608 may exhibit properties similar to that of the first magnetic element 212 and the second magnetic element 402. In this scenario, the introducer sheath 602 is inserted into the lumen 106a through the first vascular access point 108. The third magnetic element 608 is configured to exert a third magnetic force to magnetically couple with the guidewire 110 advanced into the lumen 106a through the second vascular access point. The magnetic coupling of the introducer sheath 602 and the guidewire 110 facilitates crossing of the occlusion 116 as explained above.

Various embodiments of the disclosure, as discussed above, may be practiced with steps and/or operations in a different order, and/or with hardware elements in configurations, which are different than those which, are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A medical device, comprising:
   a catheter comprising a proximal portion, a distal portion and a hollow cavity extending there between, the distal portion of the catheter configured to be deployed into a lumen of a blood vessel by advancing the catheter through a first vascular access point of a subject; and
   an elongate member comprising a distal tip portion mounted with a first magnetic element and configured to be insertable within the catheter, a region proximate to the distal tip portion mounted with the first magnetic element, formed of a softer material than the rest of the elongate member, the distal tip portion of the elongate member configured to be deployed in the lumen of the blood vessel by advancing the elongate member through the catheter deployed in the lumen of the blood vessel through the first vascular access point,
   wherein the catheter comprises an inflatable balloon located proximate to the distal portion and an expandable occlusive mesh mounted to the inflatable balloon, wherein the elongate member is configured to inflate the balloon, wherein the inflating the balloon facilitates expansion of the expandable occlusive mesh radially, thereby providing a passageway for the elongate member and a guidewire for magnetic coupling,
   wherein the first magnetic element of the elongate member is configured to exert a first magnetic force to magnetically couple with the guidewire advancing within the lumen of the blood vessel through a second vascular access point of the subject, and
   wherein a magnetic coupling of the elongate member and the guidewire facilitates attracting the guidewire into the catheter and drawing out from the first vascular access point by simultaneously withdrawing the elongate member from the first vascular access point and advancing the guidewire through the second vascular access point.

2. The medical device as claimed in claim 1, wherein the first magnetic force exerted by the first magnetic element enables the guidewire, the elongate member and the catheter to penetrate through tissue in a subintimal space of an occlusion of the blood vessel keeping the guidewire and the elongate member apart from each other for the magnetic coupling.

3. The medical device as claimed in claim 1, wherein the elongate member comprises one of a stylet, a dilator, and a needle.

4. The medical device as claimed in claim 1, wherein the catheter comprises a side hole configured at the distal portion for allowing a passageway for the elongate member deployed in the catheter.

5. The medical device as claimed in claim 4, wherein the region proximate to the distal tip portion of the elongate member, mounted with the first magnetic element, is curved or angled.

6. The medical device as claimed in claim 1, wherein the first magnetic force exerted by the first magnetic element enables the elongate member to pass through a side hole and enter the lumen of the blood vessel by penetrating through tissue in a subintimal space of the blood vessel to magnetically couple with the guidewire advanced into the lumen through the second vascular access point.

7. The medical device as claimed in claim 1, wherein the catheter comprises a second magnetic element mounted at the distal portion, the second magnetic element configured to exert a second magnetic force to magnetically couple with the guidewire advanced at least into the lumen and a subintimal space of an occlusion of the blood vessel through the second vascular access point.

8. The medical device as claimed in claim 1, further comprising:
an introducer sheath having a primary portion and a secondary portion and configured to be inserted into the blood vessel of the subject through the first vascular access point, wherein the secondary portion of the introducer sheath is mounted with a third magnetic element that is configured to exert a third magnetic force to magnetically couple with the guidewire advancing within the lumen through the second vascular access point.

9. The medical device as claimed in claim 1, wherein the first magnetic element comprises one of a rare earth metal, a ferromagnetic material, and an electromagnet.

10. The medical device as claimed in claim 1, wherein a length of the elongate member is greater than a length of the catheter to enable the elongate member to guide the catheter during placement in the lumen of the blood vessel.

11. A medical device for snaring a guidewire during endovascular procedure, the medical device comprising:
a catheter comprising a proximal portion, a distal portion and a hollow cavity extending there between, the distal portion of the catheter configured to be deployed into a subintimal space of an occlusion of a blood vessel by advancing the catheter through a first vascular access point of a subject; and
an elongate member comprising a distal tip portion mounted with a first magnetic element and configured to be insertable within the catheter, a region proximate to the distal tip portion mounted with the first magnetic element, formed of a softer material than the rest of the elongate member, the distal tip portion of the elongate member configured to be deployed in the subintimal space of the occlusion by advancing the elongate member through the catheter deployed in the subintimal space through the first vascular access point,
wherein the catheter comprises an inflatable balloon located proximate to the distal portion and an expandable occlusive mesh mounted to the inflatable balloon, wherein the elongate member mounted is configured to inflate the balloon, wherein the inflating the balloon facilitates expansion of the expandable occlusive mesh radially, thereby providing a passageway for the elongate member and the guidewire for magnetic coupling,
wherein the first magnetic element of the elongate member is configured to exert a first magnetic force to magnetically couple with the guidewire advancing within the subintimal space of the blood vessel through a second vascular access point of the subject,
wherein the first magnetic force exerted by the first magnetic element enables the guidewire, the elongate member and the catheter to penetrate through tissue in the subintimal space of the blood vessel keeping the guidewire and the elongate member apart from each other for magnetic coupling, and
wherein the magnetic coupling of the elongate member and the guidewire facilitates attracting the guidewire into the catheter and drawing out from the first vascular access point by simultaneously withdrawing the elongate member from the first vascular access point and advancing the guidewire through the second vascular access point.

12. The medical device as claimed in claim 11, wherein the elongate member comprises one of a stylet, a dilator, and a needle.

13. The medical device as claimed in claim 11, wherein the catheter comprises a side hole configured at the distal portion for allowing a passageway for the elongate member deployed in the catheter.

14. The medical device as claimed in claim 11, wherein the first magnetic force exerted by the first magnetic element enables the elongate member to pass through a side hole and enter the lumen of the blood vessel by penetrating tissue in the subintimal space of the blood vessel to magnetically couple with the guidewire advanced into the lumen through the second vascular access point.

15. The medical device as claimed in claim 11, wherein the catheter comprises a second magnetic element mounted at the distal portion, the second magnetic element configured to exert a second magnetic force to magnetically couple with the guidewire advanced at least into the lumen and the subintimal space of the occlusion through the second vascular access point.

16. The medical device as claimed in claim 11, further comprising:
an introducer sheath having a primary portion and a secondary portion and configured to be inserted into the blood vessel of the subject through the first vascular access point, where in the secondary portion of the introducer sheath is mounted with a third magnetic element that is configured to exert a third magnetic force to magnetically couple with the guidewire advancing within the lumen through the second vascular access point.

17. The medical device as claimed in claim 11, wherein the first magnetic element comprises one of a rare earth metal, a ferromagnetic material, and an electromagnet.

* * * * *